United States Patent
Grandjean et al.

(12) 
(10) Patent No.: US 6,406,421 B1
(45) Date of Patent: Jun. 18, 2002

(54) SYSTEM AND METHOD OF DETERMINING SKELETAL MUSCLE CONTRACTION BY SERIAL LEAD IMPEDANCE MEASUREMENTS

(75) Inventors: Pierre Andre Grandjean, Warsage (BE); David E. Francischelli, Anoka; Kendra K. Gealow, Mankato, both of MN (US); Robert Leinders, Bx Limbricht (NL); Martinus A. G. M. Bakx, Bc Geleen (NL); Koen J. Weijand, Eg Rockanje (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/149,021

(22) Filed: Sep. 8, 1998

(51) Int. Cl.[7] .......................... A61M 1/12; A61H 31/00; A61N 1/36

(52) U.S. Cl. ............................................. 600/17; 607/9

(58) Field of Search ............................. 600/17; 607/11, 607/9, 28

(56) References Cited

U.S. PATENT DOCUMENTS

| | | | |
|---|---|---|---|
| 3,745,990 A | 7/1973 | Neis | 128/2 S |
| 4,688,581 A | 8/1987 | Moss | 128/741 |
| 4,735,205 A | 4/1988 | Chachques et al. | 128/419 PG |
| 5,069,223 A | 12/1991 | McRae | 128/734 |
| 5,170,784 A | 12/1992 | Ramon et al. | 128/419 PG |
| 5,285,781 A | 2/1994 | Brodard | 607/59 |
| 5,344,386 A | 9/1994 | Schaldach | 600/16 |
| 5,417,717 A | 5/1995 | Salo et al. | 607/18 |
| 5,419,767 A | 5/1995 | Eggers et al. | 604/114 |
| 5,693,000 A | * 12/1997 | Crosby et al. | 600/16 |
| 5,697,952 A | 12/1997 | Francischelli et al. | 607/5 |
| 5,807,234 A | * 9/1998 | Bui et al. | 600/17 |

OTHER PUBLICATIONS

Chiu, Ray C.-J., "Using Skeletal Muscle For Cardiac Assistance," *Scientific American Science & Medicine*, Nov./Dec. 1994, pp. 68–77.

* cited by examiner

Primary Examiner—Carl H. Layno
(74) Attorney, Agent, or Firm—Thomas F. Woods; Michael J. Jaro; Harold Patton

(57) ABSTRACT

There is provided a system and method for continually monitoring the occurrence of contraction during stimulation of skeletal muscle which is employed in a cardiac assist-type system. During delivery of a periodic burst, or train of stimulus pulses, the impedance of the muscle between the electrodes through which the pulses are delivered is monitored, and evaluated to determine whether or not stimulation has been achieved. In a particular embodiment, the impedance and impedance derivative values are accumulated throughout the burst, and assessed to determine whether the impedance change corresponded to a full muscle contraction. In the event of failure to stimulate the muscle to contraction, the system can automatically adjust the pulse output parameters to achieve reliable contraction.

8 Claims, 3 Drawing Sheets

SYSTEM AND METHOD OF DETERMINING SKELETAL MUSCLE CONTRACTION BY SERIAL LEAD IMPEDANCE MEASUREMENTS

FIELD OF THE INVENTION

This invention relates generally to systems for stimulating skeletal muscle, e.g., cardiac assist systems, and more particularly augmenting such systems to provide an ongoing determination of whether the skeletal muscle is being stimulated.

BACKGROUND OF THE INVENTION

Cardiac assist systems are designed to aid patients with chronically and unacceptably low output who cannot have such cardiac output raised to an acceptable level by traditional treatments, e.g., pacing or drug therapy. A specific type of cardiac assist system to which this invention is addressed, as a preferred example, is cardiomyoplasty. Cardiomyoplasty is surgical procedure for treating chronic heart failure (CHF), whereby a patient's latissimus dorsi (LD) muscle is elevated, dissected, passed into the thoracic cavity, and then wrapped and secured around the failing heart. The LD muscle is first gradually stimulated with electrical impulses for a period of time up to about twelve weeks, to convert the muscle to a fatigue-resistant state. Following this conditioning, the LD muscle is chronically stimulated to contract in synchrony with the heart, in order to provide hemodynamic assistance. During the chronic muscle stimulation, an implantable pulse generator senses contractions of the heart via one or more sensing leads and controls generation of stimulation of the appropriate nerves of the muscle tissue with burst signals adapted to cause the muscle tissue to contract in synchrony with the heart. As a result, the heart is assisted in its contractions, thereby raising the stroke volume, and thus the output.

Following transposition of the LD muscle into the thoracic cavity, there is currently no reliable method or device for determining if the muscle is in fact contracting when stimulated. Further, contractions may be weak or strong, and there is no reliable method of determining the strength of the contractions that do take place. In the prior art, implantable sensors have been proposed and tested, with varying degrees of as of yet unfulfilled promise. The most basic sensors provide a yes/no indication of muscle contraction, while more sophisticated sensors are designed to provide a quantitative indication of relative strength of the contraction or contractility. However, such more sophisticated sensors are bulky and generally not yet proven. There thus remains a need in the art for a method and subsystem for monitoring skeletal muscle contraction on a beat-by-beat basis, so as to provide information for controlling the output level of the pulses in each stimulation pulse burst.

As is known, a unique characteristic of cardiac muscle is that it is able to be paced and fully captured by the application of a single electrical impulse. Skeletal muscle, on the other hand, will yield only a twitch contraction to a single electrical impulse. To effect a full, tetanic contraction in skeletal muscle requires delivering a train of electrical pulses to that muscle. Electrical pulses are typically delivered via a pair of leads, e.g., intramuscular, epimysial, etc., or between one lead electrode placed within or on the muscle and the pulse generator case for unipolar stimulation. It has been noted that during stimulation of the skeletal muscle, when the muscle does contract, the lead electrodes move relative to each other. As the distance between the electrodes carried by the leads changes, so does the impedance between the leads. This invention takes advantage of the relationship between muscle length and inter-lead impedance, which is known to be a substantially linear relationship. Consequently, the basis of this invention is to measure the impedance between the stimulation electrodes during each pulse in a stimulation train, and from such impedance information determine whether a contraction has occurred, and the quality of the muscle contraction.

Although the preferred embodiment of this invention is set forth with the illustration of cardiomyoplasty, it is equally applicable to other procedures, including aorta myoplasty, incontinence treatment, and any other muscle-activated system.

SUMMARY OF THE INVENTION

There is provided a system and method for stimulating skeletal muscle as part of a therapeutic procedure, which includes determining when delivered stimulation has evoked contraction of the skeletal muscle. The system provides a controllable pulse generator for periodically generating a burst of stimulus pulses and leads for delivering the bursts to electrodes in the skeletal muscle, and impedance measuring circuitry for measuring the impedance between the electrodes at the time of each pulse of the series. The impedance measurements are processed, preferably including obtaining the derivative or change in impedance for each pulse burst, and the impedance data is analyzed to determine whether it reflects a full muscle contraction. In the event of determinations of no contraction, the system includes a feedback mechanism for adjusting the power output of the burst pulses, so as to provide cyclical stimulation sufficiently above threshold to provide reliable muscle contraction.

DESCRIPTION OF THE PREFERRED EMBODIMENTS

Figure 1:
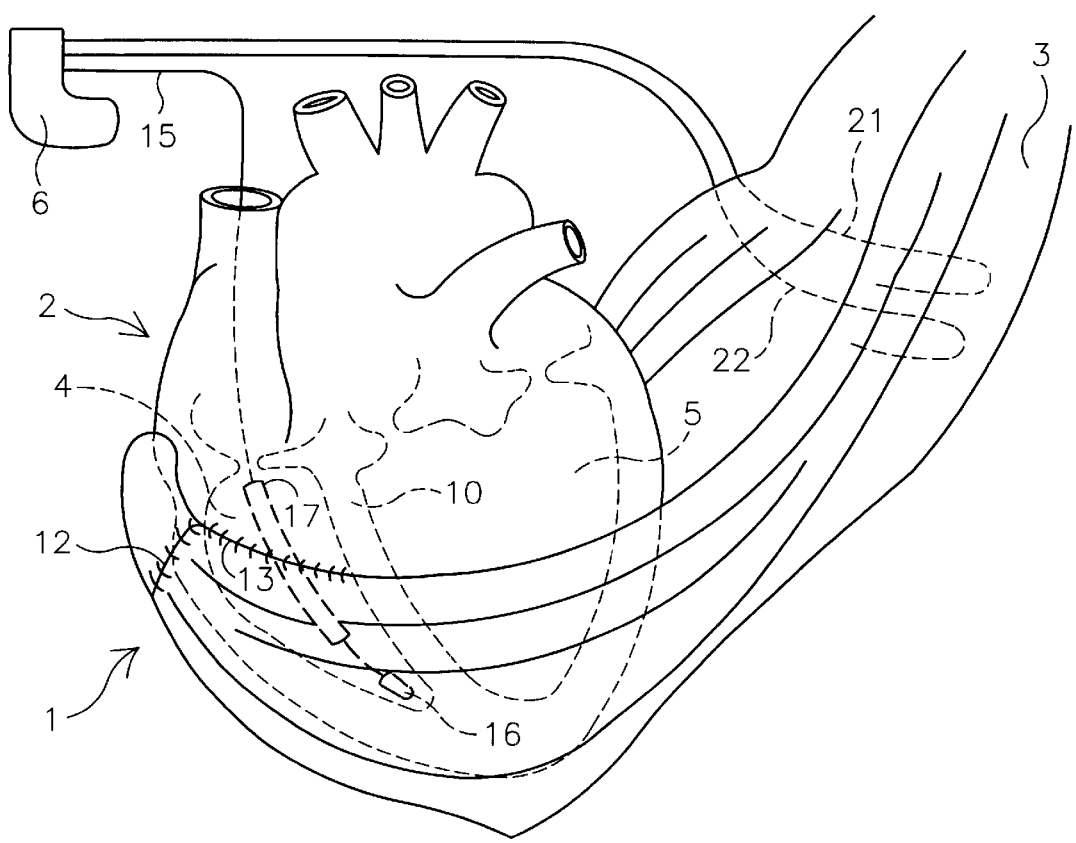
FIG. 1 is a diagrammatic representation of a system for performing chronic stimulation of a skeletal muscle for cardiac assistance using systolic augmentation, as well as direct electrical stimulation of the heart, in accordance with the present invention.

FIG. 1 illustrates an example of a system 1 for performing long-term stimulation of skeletal muscles for cardiac assistance using systolic augmentation as well as direct electrical stimulation of a heart 2. While the invention is illustrated in the environment of a cardiac assist system, a preferred embodiment, it is to be understood that it is equally applicable to other treatment systems, as noted above. As shown in FIG. 1, skeletal muscle graft 3 is positioned about the heart 2. In a preferred embodiment the latissimus dorsi muscle is used for the skeletal muscle graft, as is well known in the art. The longitudinal fibers of the muscle graft 3 are oriented generally perpendicular to the longitudinal axes of the right ventricle 4, left ventricle 5 and interventricular septum 10 of the heart. Muscle graft 3 is positioned in this manner so that when it is stimulated, muscle graft 3 compresses ventricles 4 and 5, and particularly left ventricle 5, to thereby improve the force of right and left ventricular contraction. In such a manner the overall hemodynamic output of heart 2 is increased.

In a preferred configuration, muscle graft 3 is wrapped around the heart 2 and fixedly attached to itself to form a cup-shaped "sling," using running sutures 12. Alternatively, muscle graft 3 may be attached to heart 2 using running sutures 13 as illustrated.

In the illustrated system, device 6 includes a pacemaker portion of standard form, for generating pacing pulses for delivery to the patient's heart. For applications other than cardiac assist, the device 6 is another suitable pulse generator programmed to deliver appropriate pulses. As seen, electrical stimulation and sensing of heart 2 is accomplished through lead 15. In particular, lead 15 electrically couples pacing pulses from generator 6 to heart 2, specifically to the right ventricle. Although not illustrated, the system may embody a dual chamber pacemaker subsystem, or a or 4 chamber pacemaker as is used frequently for CHF patients. Generator 6 may also provide defibrillation and/or cardioversion pulse therapies, and lead 15 has appropriate electrodes for providing cardiac pacing as well as defibrillation therapies. In the preferred embodiment lead 15 is the model 6936 tripolar TRANSVENE lead from Medtronic, Inc., Minneapolis, Minn. As illustrated, lead 15 is implanted in right ventricle 4 such that bipolar pacing electrode assembly 16 is in the right ventricular apex and defibrillation coil 17 is within the right ventricle 4. Although in the preferred embodiment a single lead is provided for pacing as well as defibrillation therapies, other types of lead configurations, such as multiple transvenous or subcutaneous or any combination thereof, may be used.

Muscle graft 3 is electrically stimulated through a pair of leads 21, 22. In particular, leads 21, 22 couple pulse generator 6 to skeletal muscle graft 3. In the preferred embodiment leads 21, 22 are the model 4750 intramuscular lead from Medtronic, Inc., Minneapolis, Minn. As seen, each lead 21, 22 extends from pulse generator 6 to latissimus dorsi muscle graft 3. The electrodes (not shown) of each lead 21, 22 are placed to cause muscle graft 3 to contract when electrically stimulated, as is well known in the art. Other types of leads or electrodes, however, may be used, such as epimysial or neuromuscular leads.

It is to be noted that although FIG. 1 shows one specific configuration, other skeletal muscle-powered cardiac assist systems may be configured in other ways. Thus, the present invention may be used in any system providing cardiac augmentation using skeletal muscles, such as aortic counter pulsation, or a skeletal muscle ventricle.

Figure 2:
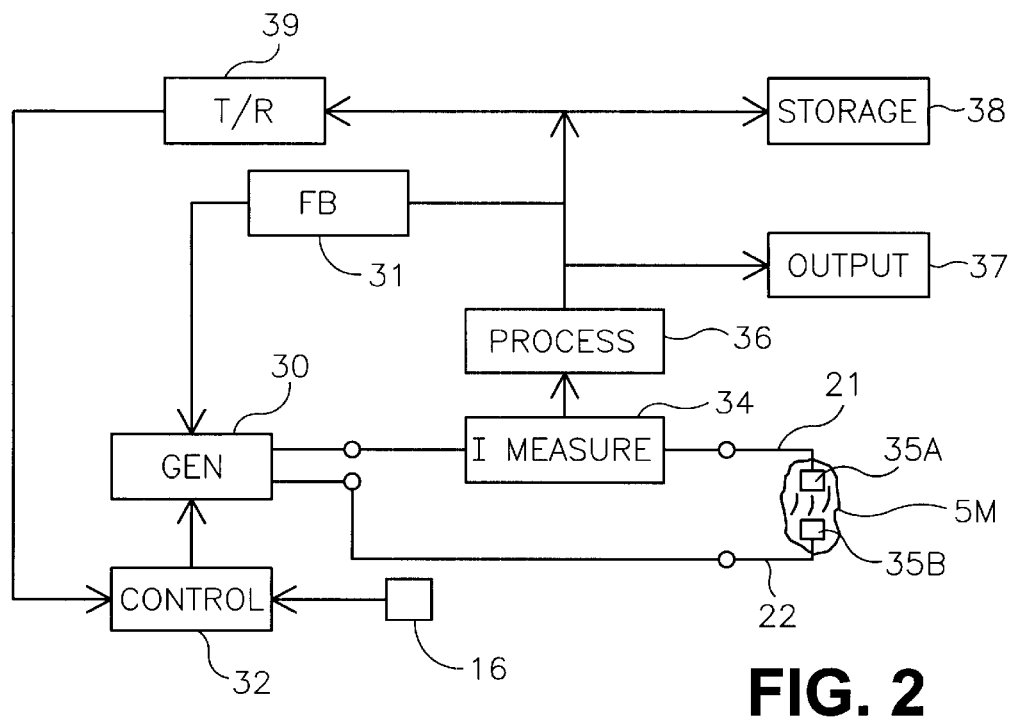
FIG. 2 is a block diagram of a skeletal muscle stimulation system in accordance with this invention, providing for continued measurement of skeletal muscle impedance during delivery of stimulation bursts.

Referring now to FIG. 2, there is shown a simplified block diagram of the primary components of pulse generator device 6, which are functional providing the stimulus bursts and in measuring skeletal muscle impedance and thus determining the presence or absence of skeletal muscle contraction. Reference is made to U.S. Pat. No. 5,697,952, assigned to Medtronic, Inc., for a more detailed description of a device which provides cardiac pacing and defibrillation, as well as stimulation of a skeletal muscle wrap.

Referring to the details of FIG. 2, a skeletal muscle generator circuit 30 is controlled by control block 32, which suitably incorporates a microprocessor and associated software, as discussed more fully in the referenced application. Generator 30 provides periodic bursts of pulses, which are synchronized with the cardiac contractions, which are sensed by electrodes 16 or coordinated with delivered pacing pulses. The generator 30 preferably provides constant voltage pulses, and measuring circuit 34 suitably uses a current measuring transistor and a sample hold circuit to obtain a measure of current flow during each pulse. The pulses of the burst are delivered on leads 21 and 22, to electrodes positioned in the skeletal muscle (SM) and identified at 35A and 35B. For each pulse of the burst, the current measure obtained by circuit 34 is processed in circuitry 36. Such processing may include normal signal processing, e.g., amplification, and also includes calculating Z by dividing the pulse voltage V by the measured current I; a measure of Z can be obtained simply by getting the inverse of I. As seen from the diagram of FIG. 2, Z represents the impedance between the electrodes, as well as the lead impedance, as is discussed further below. The processing also includes obtaining the difference ΔZ in impedance compared to the last pulse, to get a measure of dZ/dt. In a preferred embodiment, these calculations are preferably made with a microprocessor, although dedicated circuitry may also be used. Where available, e.g., at time of the surgery for providing the cardiac assist system, the measured impedance is outputted, or indicated as illustrated at 37. The impedance and dZ/dt values are also suitably stored at 38, and can be transmitted through T/R circuit 39 to an external receiver for analysis. Circuitry for telemetry transmission and receiving, shown at T/R block 39, is used to receive program commands from an external source, and connect them through to control block 32.

The processed impedance data from block 36 is also analyzed at feedback block 31, which determines whether conditions require adjustments of the power output of the stimulating pulses. Thus, if a burst fails to produce a muscle contraction, or x out of n+x bursts fail to result in full contractions, a signal is outputted to controllable generator 30, to increase one of the pulse parameters so as to augment the power out, to secure the output power level above the chronic stimulus threshold of the skeletal muscle. Block 31 suitably includes microprocessor analysis of the Z and dZ/dt data for determining whether or not the heart has contracted in response to a stimulus burst, and whether a contraction is weak or strong.

Figure 3A:
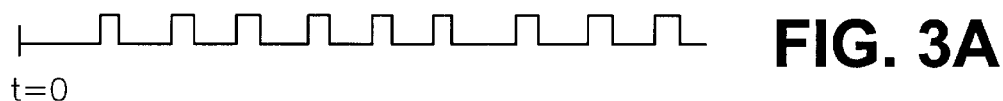
FIG. 3A is a timing diagram showing a first pulse burst wherein each pulse has an output level above the skeletal muscle threshold, and a second following burst of pulses wherein each pulse has an output level below the muscle threshold.
Figure 3B:
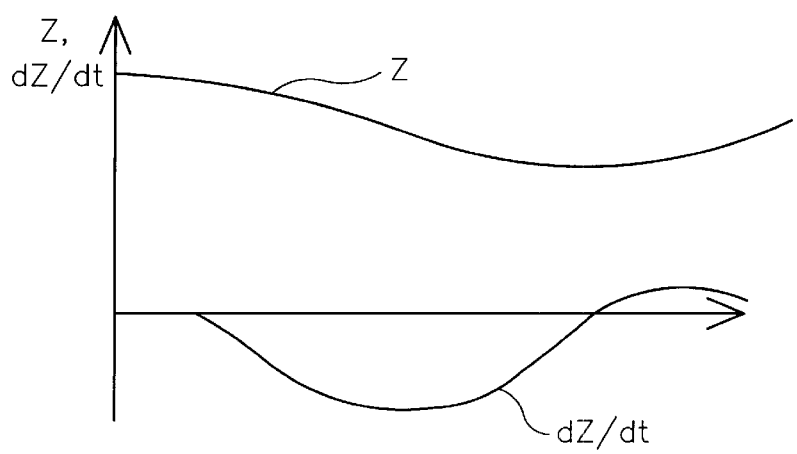
FIG. 3B is a pair of curves representing variations of impedance(Z) and dZ/dt corresponding to delivery of the stimulation burst.

Referring to FIGS. 3A and 3B, there is shown in juxtaposition, a pulse train of pulses delivered to the skeletal muscle, as well as a graph of variations of impedance and the derivative of impedance with time. As set forth above, when the stimulation burst is delivered and the muscle begins to contract, the distance between the lead electrodes changes, and so does the impedance between the lead electrodes. The impedance relationship is substantially linear with muscle length, in accordance with, for example, the following equation:

$$Z = 2.8 + 0.65L$$

where Z is impedance and L is the length between the electrodes. This equation illustrates that in the physiological range of contraction during stimulus, which is approximately 10–20 mm, an impedance change in the order of 6.5–13 ohms is expected. Assuming a coil and connector impedance of 250 ohms, this represents a 2.2–4.3% impedance change. This change in impedance is illustrated in FIG. 3B. It is noted that from time t=0 until the first pulse of the stimulus burst, impedance is substantially constant, at a level in the range of 250–300 ohms. As the pulse train continues, impedance drops, and dZ/dt increases in negative amplitude. Toward the end of the pulse train, the impedance drop diminishes, such that dZ/dt starts to rise. In the illustrated curves of FIG. 3B, a fairly sharp in Z and a pronounced detectable drop in dZ/dt is found, indicating that contraction has been achieved.

As shown in FIG. 3A, the burst suitably comprises six pulses, each separated by about 30 ms and having a pulse width of about 200 $\mu$s. The output voltage is suitably in the range of 5–6 volts, although chronic stimulation may vary from case to case. Also shown in FIG. 3A is a second shorter series of sub-threshold pulses suitably delivered at about 250–300 ms from time=0. These sub-threshold pulses are used to monitor muscle length during the relaxation phase of the contraction, and the impedance measurements taken during these sub-threshold pulses is also processed to determine the quality of the relaxation phase.

Figure 4:
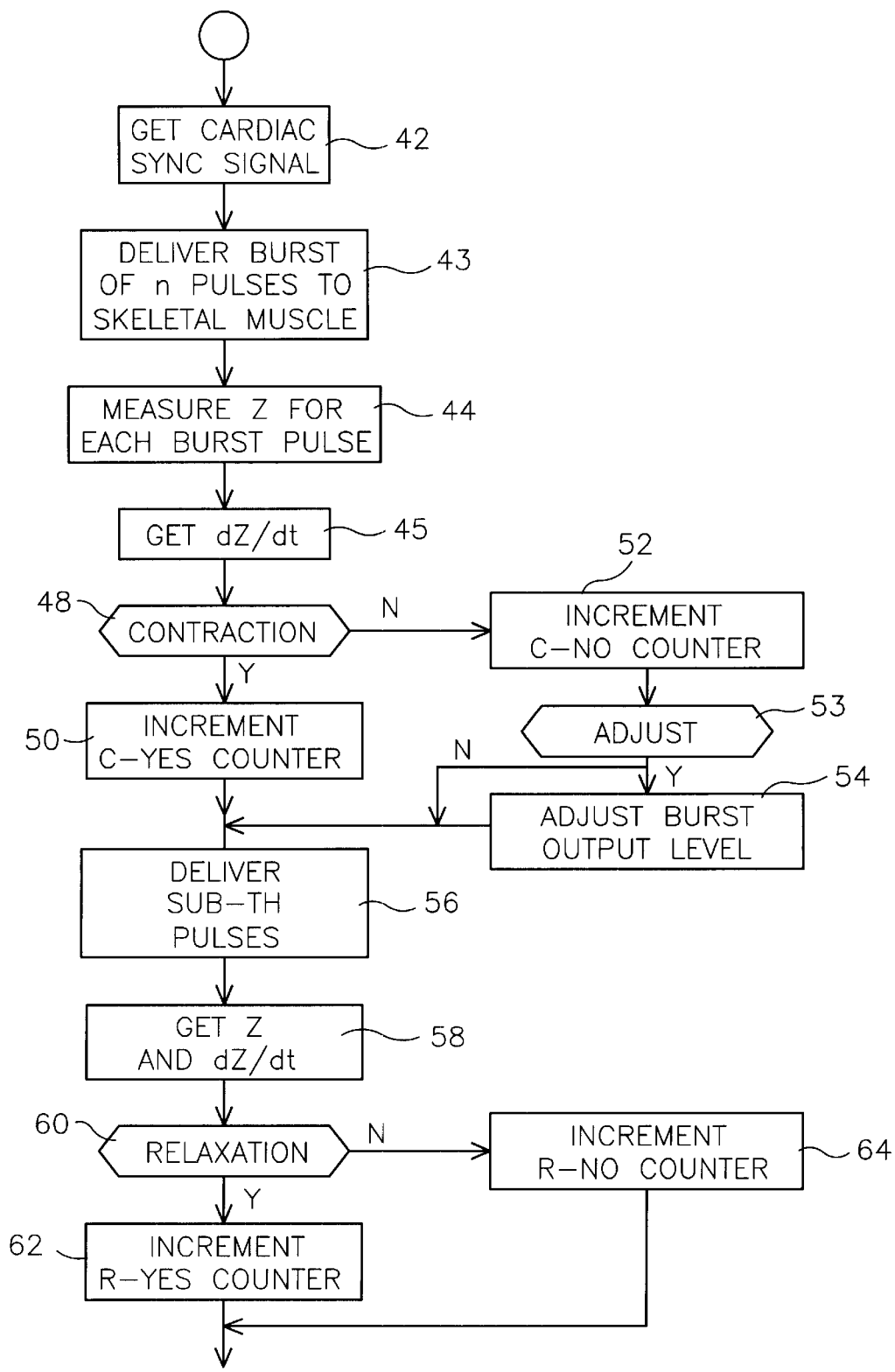
FIG. 4 is a flow diagram illustrating the primary steps carried out by the implantable system of this invention for determining when skeletal muscle has been stimulated to full contraction, and for ongoing data storage concerning muscle contractions.

Referring now to FIG. 4, there is shown a flow diagram representing the primary steps taken in carrying out the impedance measurements and determination of contraction, in accordance with a cardiac-assist embodiment of this invention. At block 42, the cardiac sync signal is obtained, as discussed above in relation to FIG. 2. Of course, for treatment applications other than cardiac assist, the sync is provided from another source, e.g., from a sync generator within device 6. At 43, in timed relation to the cardiac sync signal, a burst of n pulses is generated and delivered to the skeletal muscle. Although the invention has been illustrated with a burst of six such pulses, n is a variable which can be adjusted at time of implant, or programmed after implant. As the burst of impulses is being delivered, the impedance Z for each burst is measured and stored at 44, and dZ/dt is calculated and stored following each burst pulse, suitably by obtaining the differential impedance between pulses. Note that each impedance measurement contains a measure of the contraction of the muscle concurrent with the pulse, and the collective impedance data provides information from which the degree of contraction can be determined. At 48, following the burst delivery and obtaining the impedance data, contraction is determined as a function of the impedance data. The determination of whether or not there has been contraction, and the relative strength of the contraction, is preferably a software task carried out by a microprocessor subsystem. The invention embraces any algorithm, simple or complex, that operates on the impedance data. For example, in many cases it may be sufficient to determine how sharply dZ/dt changes following initiation of the burst, or simply the maximum drop in dZ/dt corresponding to a burst. Thus, if the maximum negative value of dZ/dt exceeds a predetermined threshold, contraction is indicated; if the negative value is within a given range below the threshold, a weak contraction is indicated, but it exceeds a second, greater threshold, a strong contraction is indicated. It is to be understood that other more complex determinations as a function of the measured impedance values may be utilized. If, at 48, it is determined that a contraction has taken place, then at 50 data reflecting this is stored, suitably by incrementing a counter designated C-YES, to obtain a running count of contractions. If it is determined that there has not been a contraction, or that the contraction is weak, then at 52 a C-NO counter is incremented. The routine then goes to 53 and determines whether an adjustment to the output level of the burst pulses should be made to raise them safely above contraction threshold. Here too, the decision may be based upon a simple or complex algorithm, e.g., a single failure to achieve contraction may warrant an adjustment or x failures out of n+x cycles may be required. If no adjustment is called for, the routine branches to block 56; if an adjustment is called for, one or more parameters of the burst pulses are adjusted at block 54.

Referring to block 56, a shorter burst of sub-threshold pulses is delivered following the stimulation burst. As indicated at 58, for each pulse of the sub-threshold burst, a measure of Z and dZ/dt is obtained. At 60, the sub-threshold impedance data is analyzed to determine whether or not there has been a physiologic relaxation. If yes, at 62 the R-YES counter is incremented; if no the R-NO counter is incremented. This data may be monitored for use in adjusting therapy.

There has thus been disclosed a system and method for making serial lead impedance measurements in a system for applying therapy by stimulating skeletal muscle. The measurements are made during each stimulation burst which is delivered to the skeletal muscle, for determining whether or not the burst achieved a satisfactory contraction. It is to be understood that variations with respect to the illustrated system and method are within the scope of the invention. For example, any convenient circuitry for determining muscle impedance can be used, e.g., constant current pulses can be used together with measurements of the differential output voltage. Of course, muscle threshold will differ from case to case, and the burst pulse and sub-threshold pulse parameters will be programmed accordingly. It is to be noted that while the preferred embodiment incorporates the simplicity of using the stimulus pulses for determining impedance, a separate impedance detection circuit using either pulses or a continuous signal may be used for monitoring impedance changes relative to the stimulus burst.

What is claimed is:

1. An implantable system for stimulating predetermined skeletal muscle in a patient to contraction, comprising a stimulus generator for generating bursts of stimulus pulses, lead means for delivering said bursts to said skeletal muscle, measuring means for determining concurrently with each pulse of said burst a measure of the contraction of said muscle, and determining means for determining from said measures whether said muscle has been stimulated to contraction, wherein said lead means comprises two electrodes positioned in said muscle, said measuring means comprises impedance moans for measuring the muscle impedance between said electrodes, and said determining means comprises algorithm means for determining contraction as a function of said impedance measurements.

2. The system as described in claim 1, further comprising processing means for obtaining the time derivative of said measured impedance, and wherein said algorithm means comprises means for determining contraction as a function of said time derivative.

3. The system as described in claim 2, wherein said algorithm means comprises strength means for determining a measure of the strength of a skeletal muscle contraction as a function of impedance measurements taken during a burst and said impedance derivative.

4. The system as described in claim 2, comprising adjustment means for adjusting the strength of said burst pulses as a function of said contraction determination over one or more stimulation cycles.

5. An implantable cardiac assist system, providing for stimulation of an LD ("latissimus dorsi") muscle wrapped around a patient's heart, comprising:

stimulus means for stimulating said muscle, said stimulus means having a pulse generator and a control circuit for controlling said pulse generator to generate a burst of pulses synchronized with each cardiac contraction;

a pair of leads, each lead having an electrode for positioning at a respective location in said muscle, said leads being connected to said pulse generator to deliver said pulses across said locations;

impedance means for obtaining serial measures the impedance between said leads corresponding to each pulse of a said burst;

determining means for determining the state of contraction of said muscle as a function of said impedance measures, and feedback means for adjusting the output level of said burst pulses as a function of the determined states of contraction, wherein said feedback means comprises means for increasing the pulse output level upon determination of a failure to contract in response to a delivered burst.

6. The system as described in claim 5, wherein said stimulus means comprises constant voltage means for generating pulses of substantially constant voltage, and said impedance means comprises current means for obtaining a measure of the current delivered to said leads with each said constant voltage pulse.

7. A method of stimulating skeletal muscle as part of a medical treatment, said method including determining whether said stimulating results in contractions of the skeletal muscle, comprising:

generating bursts of stimulus pulses, delivering said bursts to said muscle between two predetermined points in said muscle;

determining, substantially concurrently with each said burst, a measure of the contraction of said muscle BY measuring the impedance between said two points at the time of each said delivered pulse of each said burst;

analyzing when said muscle has contracted in response to said delivered bursts, and adjusting the strength of said pulses as a function of said analyzing, and increasing the output level of said burst pulses upon determination of a failure of muscle contraction in response to a said delivered burst.

8. The method as described in claim 7, further comprising:

delivering said bursts to skeletal muscle wrapped around a patient's heart to provide cardiac assist;

delivering said bursts between two predetermined points on said skeletal muscle;

determining the impedance between said points corresponding to each delivered pulse;

determining a measure of the derivative of said impedance measurements, and determining the state of muscle contraction as a function of said impedance measurements and said impedance derivative.

\* \* \* \* \*